US007164023B2

(12) United States Patent
Deshpande et al.

(10) Patent No.: US 7,164,023 B2
(45) Date of Patent: *Jan. 16, 2007

(54) BENZOQUINOLIZINE-2-CARBOXYLIC ACID ARGININE SALT TETRAHYDRATE

(75) Inventors: Prasad K. Deshpande, Aurangabad (IN); Vijaya N. Desai, Aurangabad (IN); Ravindra D. Yeole, Aurangabad (IN); Shrikant V. Gupte, Aurangabad (IN); Mahesh V. Patel, Aurangabad (IN); Noel J. de Souza, Mumbai (IN)

(73) Assignee: Wockhardt Limited, Aurangabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/749,932

(22) Filed: Dec. 31, 2003

(65) Prior Publication Data
US 2005/0054666 A1    Mar. 10, 2005

(30) Foreign Application Priority Data
Sep. 4, 2003    (IN) .................. 915/MUM/2003

(51) Int. Cl.
C07D 401/04    (2006.01)
C07D 401/14    (2006.01)

(52) U.S. Cl. ........................ 546/95; 546/94; 514/294
(58) Field of Classification Search ................. 514/294; 546/95, 94
See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuewes et al. |
| 3,924,042 A | 12/1975 | Gerster et al. |
| 3,984,403 A | 10/1976 | Fujisawa et al. |
| 3,985,882 A | 10/1976 | Gerster et al. |
| 4,008,719 A | 2/1977 | Theeuwes et al. |
| 4,051,247 A | 9/1977 | Schuppan et al. |
| 4,382,892 A | 5/1983 | Hayakawa et al. |
| 4,399,134 A | 8/1983 | Ishikawa et al. |
| 4,404,207 A | 9/1983 | Stern et al. |
| 4,416,884 A | 11/1983 | Ishikawa et al. |
| 4,443,447 A | 4/1984 | Gerster et al. |
| 4,472,406 A | 9/1984 | Gerster et al. |
| 4,472,407 A | 9/1984 | Stern et al. |
| 4,535,161 A | 8/1985 | Hayakawa et al. |
| 4,552,879 A | 11/1985 | Ishikawa et al. |
| 4,563,459 A | 1/1986 | Groher et al. |
| 4,594,347 A | 6/1986 | Ishikawa et al. |
| 4,599,418 A | 7/1986 | Irikura et al. |
| 4,638,067 A | 1/1987 | Culbertson et al. |
| 4,642,355 A | 2/1987 | Nakamura et al. |
| 4,665,079 A | 5/1987 | Culbertson et al. |
| 4,777,175 A | 10/1988 | Culbertson et al. |
| 4,822,801 A | 4/1989 | Domagala et al. |
| 4,874,764 A | 10/1989 | Ueda et al. |
| 4,880,806 A | 11/1989 | Ueda et al. |
| 4,894,458 A | 1/1990 | Masuzawa et al. |
| 4,935,420 A | 6/1990 | Ueda et al. |
| 4,997,943 A | 3/1991 | Iwata et al. |
| 5,051,509 A | 9/1991 | Nagano et al. |
| 5,097,032 A | 3/1992 | Domagala et al. |
| 5,185,337 A | 2/1993 | Fujii et al. |
| 5,290,934 A | 3/1994 | Ueda et al. |
| 5,348,961 A | 9/1994 | Iwata et al. |
| 5,420,140 A | 5/1995 | Perrin |
| 5,436,367 A | 7/1995 | Iwata et al. |
| 5,607,942 A | 3/1997 | Petersen et al. |
| 5,639,886 A | 6/1997 | Zerbes et al. |
| 5,677,316 A | 10/1997 | Ao et al. |
| 5,859,026 A | 1/1999 | Ito et al. |
| 5,869,661 A | 2/1999 | Ochi et al. |
| 5,889,009 A | 3/1999 | Miyake et al. |
| 6,034,100 A | 3/2000 | Adachi et al. |
| 6,121,285 A | 9/2000 | Takemura et al. |
| 6,136,806 A | 10/2000 | Hittel |
| 6,184,388 B1 | 2/2001 | Takemura et al. |
| 6,329,391 B1 | 12/2001 | Ledoussal et al. |
| 6,514,986 B1 | 2/2003 | de Souza et al. |
| 6,664,267 B1 * | 12/2003 | de Souza et al. ........... 514/294 |

FOREIGN PATENT DOCUMENTS

| | | |
|---|---|---|
| EP | 0241206 | 10/1987 |
| EP | 0287951 | 10/1988 |
| EP | 0300735 | 1/1989 |

(Continued)

OTHER PUBLICATIONS

Asahina, Y. et al. "Recent advances in structure activity relationships in new quinolones", *Prog. Drug Res.* (1992), 38: 57-106.
Japanese patent application 6-145167, dated May 24, 1994.
Cooper, C.S. et al. "Preparation and in Vitro and in Vivo Evaluation of Quinolones with Selective Activity against Gram Positive Organisms", *J. Med. Chem.* 1392-1398.
English abstract of WO 98/58923, dated Dec. 30, 1998.
English abstract of WO 94/14794, dated Jul. 7, 1994.
Chemical Abstracts 136:147733.
Chemical Abstracts 134:141378.
Chemical Abstracts 134:141377.
Chemical Abstracts 135: 300896.
Chemical Abstracts 130: 322834.

(Continued)

*Primary Examiner*—Charanjit S. Aulakh
(74) *Attorney, Agent, or Firm*—Ladas and Parry LLP (57) ABSTRACT

The invention relates to crystalline S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate, a process for its preparation and pharmaceutical formulations incorporating it as the active ingredient for use in treating microbial infections.

11 Claims, 7 Drawing Sheets

FOREIGN PATENT DOCUMENTS

| | | |
|---|---|---|
| EP | 0304087 | 2/1989 |
| EP | 0230295 | 7/1989 |
| EP | 0342675 | 11/1989 |
| EP | 0541086 | 5/1993 |
| EP | 0572259 | 12/1993 |
| EP | 0394553 | 6/1995 |
| EP | 0908181 | 4/1999 |
| EP | 0919553 | 6/1999 |
| JP | 57081486 | 5/1982 |
| JP | 57176987 | 10/1982 |
| JP | 58090511 | 5/1983 |
| JP | 63192753 | 8/1988 |
| JP | 02131483 | 5/1990 |
| JP | 02188570 | 7/1990 |
| JP | 02188589 | 7/1990 |
| JP | 05339238 | 12/1993 |
| JP | 6-145167 | 5/1994 |
| WO | 9414794 | 7/1994 |
| WO | 9415938 | 7/1994 |
| WO | 9420105 | 9/1994 |
| WO | 9724128 | 7/1997 |
| WO | 9731000 | 8/1997 |
| WO | 9744034 | 11/1997 |
| WO | 98/58923 | 12/1998 |
| WO | 9858923 | 12/1998 |
| WO | 9914214 | 3/1999 |
| WO | 9926940 | 6/1999 |
| WO | 0018404 | 4/2000 |
| WO | 00/68229 | 11/2000 |
| WO | 0068229 | 11/2000 |
| WO | 01/85095 | 11/2001 |
| WO | 0185095 | 11/2001 |
| WO | 0185728 | 11/2001 |
| WO | 02/09758 | 2/2002 |
| WO | 0209758 | 2/2002 |
| WO | 03/099815 | 12/2003 |

OTHER PUBLICATIONS

Chemical Abstracts 129:339430.
Chemical Abstracts 129:310840.
Chemical Abstracts 129:245024.
Chemical Abstracts 129: 239390.
Chemical Abstracts 127: 358825.
Chemical Abstracts 123: 164953.
Chemical Abstracts 124: 86783.
Chemical Abstracts 124: 170377.
Chemical Abstracts 124:343084.
Chemical Abstracts 127: 302924.
Chemical Abstracts 131: 153420.
Chemical Abstracts: 136:2738.
European Patent Specification 0394553 B1, dated Jun. 21, 1995.
Alsina J. et al. "Active Carbonate Resins for Solid-Phase Synthesis Through the Anchoring of a Hydroxyl Function. Synthesis of Cyclic and Alcohol Peptides", *Tetrahedron Letters*, (1997), 38(5): 883-886.
Edwards W.B. et al. "Generally Applicable, Convenient Solid-Phase Synthesis and Receptor Affinities of Octreotide Analogs", *J. Med. Chem.*, (1994), 37(22): 3749-3757.
Dhople, A.M. and M.A. Tbanez. "*In vivo* susceptibility of mycobacterium leprae to ofloxacin either singly or in combination with Rifampicin and Rifabutin", *Arzneimittel-Forschung,*, (1994), 44(4): 563-565.
Haustein U.F. et al. "Topical quinolone nadifoloxacin (OPC-7251) in bacterial skin disease: clinical evaluation in a multicenter open trial and in vitro antimicrobiological susceptibility testing", *J. Dermatological Treatment*, (1997), 8: 87-92.
Hashimoto, Koji et al. "A Practical Synthesis of (S)-(-)-Nadifloxacin: Novel Acid-Catalyzed Racemization of Tetrahydroquinaldine Derivative", *Chem. Pharm. Bull.*, (1996), 44(4): 642-645.

Irish, D. et al. "Control of an outbreak of an epidemic methicillin-resistant Staphylococcus aureus also resistant to mupirocin", *J. Hospital Infection*, (1996), 39: 19-26.
Kido, M. et al. "Crystal Structures of Nadifloxacin Anhydride and its Hemihydrate". *Chem. Pharm. Bull.*, (1994), 42(4):872-876.
Takahashi et al. "Reduction of in vitro Clastogenecity Induced by the Mixture of Optical Isomers of Nadifloxacin during Storage", *Arzneim.-Forsch./Drug Res.*, (1995), 45(1): 195-197.
Sloan et al. "Definition and attainment of high purity of organic compounds", Chapter 2, 179-182, *Physics and Chemistry of the Organic Solid State*, eds. D. Fox, Labes and Weissberer. Interscience Publishers, London. 1963.
Morita, S. et al. "An efficient synthesis of a key determinate towards (S)-(-)-Nadifloxacin", *Tetrahedron: Asymmetry*, (1995), 6(1): 245-254.
Morita, S. et al. "Synthesis and Antibacterial Activity of the Metabolites of 9-Fluoro-6,7-dihydro-8-(4-hydroxy-1-piperidyl)-5-methyl-1-oxo-1$H$,5$H$-benzo[$i,j$]quinolizine-2-carboxylic acid (OPC-7251)", *Chem. Pharm.Bull.*, (1990), 38(7): 2027-2029.
Ishikawa, H. et al. "Studies on Antibacterial agents. I. Synthesis of Substituted 6,7-Dihydro-1-oxo-1$H$,5$H$-benzo[$i,j$]-quinolizine-2-carboxylic acids", *Chem. Pharm. Bul.*, (1989), 37(8): 2103-2108.
English translation of Yamada, Hirao et al. "Evaluation of the *in vitro* drug efficacy of Nadifloxacin Cream", *Iyakuhin Kenkyu*, (2000), 31 (8): 519-524.
English abstract of Japanese patent 02131483, dated May 21, 1990.
English abstract of Japanese patent 02188589, dated Jul. 24, 1990.
English translation of Yamada, Hiroaki, et al. "Bioequivalency of 1% Nadifloxacin lotion and 1% of Nadifloxacin cream", *Iyakuhin Kenkyu*, (2000), 31(8): 525-528.
Berge, Stephen M. et al. "Pharmaceutical Salts", *J. Pharmaceutical Sciences*, (1977), 66(1): 1-19.
Abstract of Koike, M. et al. *Iyakuhin Kenkyu*, (1990), 21(5): 998-1021.
Abstract of Koike, M. et al. *Iyakuhin Kenkyu*, (1990), 21(5): 1022-1033.
Abstract of Fujita, S. et al. *Iyakuhin Kenkyu*, (1990), 21(6): 1156-1176.
Abstract of Koike, M. et al. *Yakubutsu Dotai*, (1990), 5(2): 199-208.
Abstract of Yasuo, A. et al. *Yakuri to Chiryo*, (1990), 18(4): 1717-1730.
Abstract of Hayakawa, R. et al. *Hifu*, (1990), 32(2): 217-230.
Abstract of Asada, Y. et al. *Yakuri to Chiryo*, (1990), 18(4): 1717-1730.
Abstract of Awogi, T. et al. *Iyakuhin Kenkyu*, (1990), 21(4): 626-635.
Abstract of Matsuzawa, A. et al. *Iyakuhin Kenkyu*, (1990), 21(4): 636-646.
Abstract of Nagao, T. et al. *Iyakuhin Kenkyu*, (1990), 21(4): 647-662.
English abstract of WO 97/44034, dated Nov. 27, 1997.
English abstract of JP 5339238, dated Dec. 21, 1993.
English abstract of JP 58090511, dated May 30, 1983.
Abstract of Matsuzawa, A. et al. *Iyakuhin Kenkyu*, (1990), 21(4): 663-670.
Abstract of Hashimoto, K. et al. *Iyakuhin Kenkyu*, (1990), 21(4): 671-677.
Abstract of Furukawa, M. et al. *Iyakuhin Kenkyu*, (1990), 21(5): 989-997.
Abstract of Yoshimura, S. et al. *Iyakuhin Kenkyu*, (1990), 21(5): 1034-1052.
English abstract of JP 63192753, dated Aug. 10, 1988.
English abstract of JP 57081486, dated May 21, 1982.
English abstract of JP 57176987, dated Oct. 30, 1982.
Abstract of Nakagiri, N. et al. *Iyakuhin Kenkyu*, (1990), 21(6): 1144-1155.
Abstract of Aoki, M. et al. *Iyakuhin Kenkyu*, (1990), 21(6): 1177-1202.
Abstract of Matsuzawa, A. et al. *Iyakuhin Kenkyu*, (1991), 22(1): 61-76.
Abstract of Kurokawa, I. et al. *J. Am. Acad. Dermatol.*, (1991), 25(4): 674-681.
English abstract of JP 02188570, dated Jul. 24, 1990.

Abstract of Bojar, R.A. et al. *Journal of Invesitgative Dermatology,* (1994), 103(3): 405.
Abstract of Smith, C.M. *Journal of Investigative Dermatology,* (1997), 108(3): 123.
Abstract of Hayakawa, R. et al. *Hifu,* (1998), 40(2): 165-171.
Abstract of Fujio, N. et al. *Yakuri to Chiryo,* (1998), 26(7): 1119-1132.
Kido, M. et al. "the Absolute Configuration of (R)-(+)-Nadifloxacin", *Chem. Pharm. Bull.,* (1996), 44(2): 421-423.
Miller, M.A. et al. "Development of Mupirocin Resistance Among Methicillin-Resistant *Staphylococcus aureus* After Widespread Use of Nasal Mupirocin Ointment", *Infection Control and Hospital Epidemiology,* (1996), 17(12): 811-813.
English abstract of WO99/26940, dated Jun. 3, 1999.
Mateu-de-Antonio, E.M. and M. Martin. "In vitro efficacy of several antimicrobial combinations against *Brucella Canis* and *Brucella mlitensis* strains isolated from dogs", *Veterinary Microbiology,* (1995), 45: 1-10.
Nishijima, S. et al. "Sensitivity of *Staphylococcus aureus,* Isolated from Skin Infections in 1994, to 19 Antimicrobial Agents", *J. International Medical Research,* (1995), 23: 328-334.
Nishijima, S. et al. "Activity of Eight Fluoroquinolones against Both Methicillin-Susceptible and-Resistant *Staphylococcus aureus* Isolated from Skin Infections", *J. Dermatology,* (1995), 22: 153-155.
Nishijima, S. et al. "Activity of Nadifloxacin Against Methicillin-Resistant *Staphylococcus aureus* Isolated from Skin Infections: Comparative Study with Seven Other Fluoroquinolones", *J. International Medical Research,* (1996), 24: 12-16.
Nishijima, S. et al. "Sensitivity of *Staphylococcus aureaus* and *Streptococcus pyogenes* Isolated from Skin Infections in 1992 to Antimicrobial Agents", *J. Dermatology,* (1994), 21: 233-238.
Abstract of Kurokawa, I. et al. *European Journal of Dermatology,* (1999), 9(1): 25-28.
Abstract of Komagata, Y. et al. *Japanese Journal of Antibiotics,* (1998), 51(2): 130-136.
Abstract of Gollnick, H. et al. *Dermatology,* (1998), 196(1): 119-125.
Abstract of Nishijima, S. et al. *J. International Medical Research,* (1997), 25(4): 210-213.
Abstract of Akamatsu, H. et al. *J. International Medical Research,* (1995), 23(1): 19-26
Abstract of Takahashi, N. et al. *Arzneimittel-Forschung,* (1995), 45(2): 195-197
Abstract of Takahashi, N. et al. *Arzneimittel-Forschung,* (1994), 44(11): 1265-1268.
Abstract of Patel,M.V et al. 39th IICAAC at San Diego, (Sep. 26-29, 1999) Poster No. FO558.
Chemical Abstract: Doc. No. 123-334723. Vogt, K. et al. *Drugs* (1995), 49 (Supp.2): 266-268.
Chemical Abstract: Doc. No. 123:334716. Nishijima, S. et al. *Drugs* (1995), 49 (Supp.2): 230-232.
Chemical Abstract: Doc. No. 124: 21098. Bojar, R.A. et al. *Drugs* (1995), 49 (Supp.2): 164-167.
Chemical Abstract: Doc. No. 122:213914. Morita, S. et al. *Tetrahedron: Asymmetry* (1995), 6(1): 245-254.
Chemical Abstract: Doc. No. 119: 4810. Vogt, K. et al. *Eur. J. Clin. Microbiol. Infect. Dis.* (1992), 11(10): 943-945.
Chemical Abstract: Doc. No. 113:231188. Morita, S. et al. *Chem. Pharm. Bull.* (1990), 38(7): 2027-2029.
Chemical Abstract: Doc. No. 112: 2292223. Muto, N. et al. *J. Immunoassay* (1990), 11(1): 1-16.
Japanese patent 6-145167, dated May 24, 1994.
Chemical Abstract: Doc. No. 112: 191305. Koike, M. et al. *J. Chromatogr.* (1990), 526(1): 235-239.
Chemical Abstract: Doc. No. 112: 178631. Ishikawa, H. et al. *Chem. Pharm. Bull.* (1989), 37(8): 2103-2108.
Chemical Abstract: Doc. No. 112:52083. Kawabata, S. et al. *Chemotherapy* (1989), 37(9): 1160-1178.
Abstract of Iwahara, K. et al. *European Journal of Dermatology,* (1999), 9(4): 276-277.
Abstract of Radl, S. *Archiv der Pharmazie,* (1996), 329(3): 115-119.
Abstract of Andriole, V.T. *Drugs,* (1993), 46 (Supp.3): 1-7.
Ball, Peter. "The Quinolones: History and Overview", Chapter 2, pp. 1-28. *The Quinolones.* Second Edition. Academic Press, 1998.
Domagala, John M. "Structure-activity and structure-side-effect relationships for the quinolone antibacterials", *J. Antimicrobial Chemotherapy* (1994), 33: 685-706.
Suto, M.J. et al. "Fluoroquinolones: Relationships between Structural Variations, Mammalian Cell Cytotoxicity and Antimicrobial Activity", *J. Med. Chem.,* (1992), 35: 4745-4750.
Abstract of Yamakawa, T. et al. *J. Antimicrobial Chemotherapy,* (2002), 49(3): 455-465.
Hooper, David C. "Mechanisms of fluoroquinolone resistance", *Drug Resistance Update,* (1999), 2: 38-55.
Ince, Dilek and David C. Hooper. "Mechanisms and Frequency of Resistance to Gatifloxacin in Comparison to AM-1121 and Ciprofloxacin in *Staphylococcus aureus*", *Antimicrobial Agents and Chemotherapy,* (2001), 45(10): 2755-2764.
Fournier, B. and David C. Hooper. "Mutations in Topoisomerase IV and DNA Gyrase of *Staphylococcus aureus*: Novel Pleiotropic Effects on Quinolone and Coumarin Activity", *Antimicrobial Agents and Chemotherapy,* (1998), 42(1): 121-128.
Zhao, Xilin et al. "Killing of *Staphylococcus aureus* by C-8-Methoxy Fluoroquinolones", *Antimicrobial Agents and Chemotherapy,* (1998), 42(4): 956-958.
Breines, David M. et al. "Quinolone Resistance Locus *nfxD* of *Escherichia coli* Is a Mutant Allele of the *parE* Gene Encoding a Subunit of Topoisomerase IV", *Antimicrobial Agents and Chemotherapy,* (1997), 41(1): 175-179.
Fournier, B. and David C. Hooper. "Expression of the Multidrug Resistance Transporter NorA from *Staphylococcus aureus* Is Modified by a Two-Componenet Regulatory System", *J. Bacteriology,* (2000), 182(3): 664-671.
Mandell, Lionel A. et al. "Antimicrobial Safety and Tolerability: Differences and Dilemmas", *CID,* (2001), 32 (Suppl.1): S72-S79.
Gootz, Thomas D. and Katherine E. Brighty. "Chemistry and Mechanism of Action of the Quinolone Antibacterials", Chapter 2, pp. 29-80. *The Quinolones,* Second Ed. Academic Press, 1998.
Takenouchi, T. et al. "Hydrophilicity of Quinolones Is Not an Exclusive Factor for Decreased Activity in Efflux-Mediated Resistant Mutants of *Staphylococcus aureus*", *Antimicrobial Agents and Chemotherapy,* (1996), 40(8): 1835-1842.
Zhao, Xilin et al. "DNA topoisomerase targets of the fluoroquinolones: A strategy for avoiding bacterial resistance", *Proc. Natl. Acad. Sci. USA,* (1997), 94: 13991-13996.
Takei, M. et al. "Target Preference of 15 Quinolones against *Staphylococcus aureus,* Based on Antibacterial Activities and Target Inhibition", *Antimicrobial Agents and Chemotherapy,* (2001), 45(12): 3544-3547.
Ince, Dilek and David C. Hooper. "Mechanisms and Frequency of Resistance to Premafloxacin in *Staphylococcus aureus*: Novel Mutations Suggestions Novel Drug-Target Interactions", *Antimicrobial Agents and Chemotherapy,* (2000), 44(12): 3344-3350.
Oizumi, Nobuyuki et al. "Relationship between mutations in the DNA gyrase and topoisomerase IV genes and nadifloxacin resistance in clinically isolated quinolone-resistant *Staphylococcus aureus*", *J. Infect. Chemother.,* (20010), 7: 191-194.
Jaén-Oltra, José et al. "Artificial Neural Network Applied to Prediction of Fluoroquinolone Antibacterial Activity by Topological Methods", *J. Med. Chem.,* (2000), 43: 1143-1148.
Chu, Daniel T. W. et al. "Synthesis and Structure-Activity Relationships of Novel Arylfluoroquinolone Antibacterial Agents", *J. Med. Chem.,* (1985), 28: 1558-1564.
Neu, Harold C. et al. "In Vitro Activity of Fleroxacin in Combination with Other Antimicrobial Agents", *The American Journal of Medicine,* (1993), 94 (Suppl. 3A): 3A-15S.
Chin, N. X. and H. C. Neu. "Combination of Ofloxacin and Other Antimicrobial Agents", *Journal of Chemotherapy,* (1990), 2(6):343-347.

Van der Auwera, P. et al. "Comparative *In Vitro* Activity of Ci 934, A New Fluoroquinolone, Alone and in Combination with Coumermycin Against Gram-Positive Bacteria", *Drugs Exptl. Clin,. Res.,* (1987), XIII(3): 125-132.

Asahina, Y. et al. "Recent advances in structure activity relationships in new quinolones", *Prog. Drug Res.,* (1992): 57-106.

Udo, E. E. et al. "Emergence of high-level mupirocin resistance in methicillin-resistant *Staphylococcus aureus* in Western Australia", *J. Hospital Infection,* (1994), 26: 157-165.

Bundgaard, Hans. "Design of prodrugs:Bioreversible derivatives for various functional groups and chemical entities", Chapter 1, pp. 1-5. *Design of Prodrugs.* Hans Bundgaard, editor. Elsevier Science publishers, 1985.

Mergler, M. et al. "Proceedings of the 12th American Peptide Symposium", reference cited on page 2 of EPA 09 53577.

* cited by examiner

FIG.1 ORTEP View of the molecular structure with numbering system

FIG.2  Hydrogen bonding of the water molecules

FIG. 3  X-ray powder diffraction (XRPD) spectrum of the tetrahydrate of the invention.

FIG. 4 X-ray powder diffraction (XRPD) spectrum of conversion of monohydrate to tetrahydrate.

FIG.5 Differential scanning calorimetric (DSC) analysis of the tetrahydrate of the invention FIG. 7 Theoretical XRPD spectrum of a tetrahydrate of the invention

BENZOQUINOLIZINE-2-CARBOXYLIC ACID ARGININE SALT TETRAHYDRATE

FIELD OF THE INVENTION

The present invention relates to crystalline S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate and to processes for producing it. Compositions incorporating the tetrahydrate to provide formulations for use in the prophylaxis and/or treatment of microbial infectious diseases are also described.

BACKGROUND OF THE INVENTION

S-(−)-9-Fluoro-6,7-dihydro-8-(4-hydroxypiperidin-1-yl)-5-methyl-1-oxo-1H,5H-benzo[i,j]quinolizine-2-carboxylic acid L-arginine salt is a broad-spectrum antibiotic, medically grouped together with the fluoroquinolone class of antibiotics, which is disclosed and claimed in our U.S. Pat. No. 6,514,986 B2 as being isolated in a less crystalline anhydrate form and a more crystalline hydrate form. Our U.S. Pat. No. 6,664,267 describes a crystalline monohydrate form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt that is disclosed as having advantages over the anhydrate and hydrate forms described in U.S. Pat. No. 6,514,986 B2. Such advantageous properties for the crystalline monohydrate form, in comparison to the less crystalline anhydrate and hydrate forms, include enhanced stability at specified conditions of humidity and temperature.

In accordance with the present invention, it has been found that S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate in highly homogeneous form is advantageous over previously known forms and may be usable to prepare stable pharmaceutical dosage forms, including an aqueous solution, because it is the most physically stable form and does not have a tendency over time to convert to other crystalline forms.

SUMMARY OF THE INVENTION

In accordance with the present invention, there is provided a crystalline S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate which is highly homogeneous in regard to other solvatomorphic forms thereof and has superior properties in comparison to such other anhydrate or hydrate solvatomorphic noncrystalline or crystalline forms.

The present invention further pertains to processes for the preparation of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate, pharmaceutical compositions containing it, and the use thereof in the treatment and/or prevention of a wide variety of microbial infections.

The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate of the invention is a compound that shows potent antibacterial activity against gram-positive bacteria, gram-negative bacteria and anaerobic bacteria, as described in more detail below.

DETAILED DESCRIPTION OF THE INVENTION

In accordance with the present invention, there is provided a novel highly homogeneous crystalline tetrahydrate hydratomorphic form of the broad spectrum antibiotic S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt, represented by the following structure:

S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt has been shown in mammals to be effective against a broad spectrum of microorganisms including antibiotic-resistant strains of *Staphylococcus aureus*, more particularly glycopeptide-resistant staphylococci, and to possess excellent overall tolerability. (Posters F-535, F-537, F-538, F-539, and F-540 presented at 41$^{st}$ ICAAC 2001, Chicago, Ill., USA and Poster F-564 presented at 42$^{nd}$ ICAAC 2002, San Diego, Calif., USA).

Initial methods to prepare S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt as a bulk active ingredient resulted in an anhydrate solvatomorphic form and a hydrated solvatomorphic form thereof. The physicochemical characteristics of these solvatomorphs are described in U.S. Pat. No. 6,514,986 B2. Solvatomorphism is said to exist when a molecule displays an ability to crystallize in different structures that in turn differ in their solvation state (Brittain, Spectroscopy, (2000), 15 (7), 34–39). A hydratomorph may be defined as a solvatomorph in which the solvent is water. Further investigation in the preparation of bulk material revealed that a crystalline form could be produced of a monohydrate of S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt. The physicochemical characteristics are described in our U.S. Pat. No. 6,664,267. Further investigation of processes to prepare this monohydrate and single crystals of it led to a hydratomorph which on X-ray crystallographic analysis showed it, surprisingly, to be a tetrahydrate, the detailed data for which is provided below and in the illustrations. An in-depth study of the different hydrates of S-(−)-9-fluoro-6, 7-dihydro-8-(4-hydroxypiperidin-1-yl)-5-methyl-1-oxo-1H, 5H-benzo[i,j]quinolizine-2-carboxylic acid L-arginine salt in respect of their respective x-ray diffractograms, differential scanning calorimetry graphs, their water content, their stability order as a function of temperature and/or humidity led to an understanding that the tetrahydrate is the most stable polymorph.

S-(−)-9-Fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate is further characterized by crystal parameters from single crystal x-ray crystallographic analysis as set forth below.

The crystal of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt is found to form a molecular assembly having a composition of $C_{19}H_{21}N_2O_4F \cdot C_6H_{14}N_4O_2 \cdot 4H_2O$; a 1:1 complex of S-(−)-9-fluoro-6,7-dihydro-8-(4-hydroxypiperidin-1-yl)-5-methyl-1-oxo-1H,5H-benzo[i,j]quinolizine-2-carboxylic acid and L-arginine with four water molecules of crystallization. The salt exists in the zwitterionic form in the orthorhombic system, space group $P2_12_12_1$. The details of data collection, structure solution and refinement are given in Table 1.

TABLE 1

Single Crystal Parameters of S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

| DATA | Compound of the invention |
| --- | --- |
| Formula | $C_{19}H_{21}N_2O_4F \cdot C_6H_{14}N_4O_2 \cdot 4H_2O$ |
| Formula weight | 606.64 |
| Temperature/K | 293(2) |
| Wavelength | $MoK_\alpha$ |
| Crystal system | Orthorhombic |
| Space Group | $P2_12_12_1$ |
| a/Å | 8.475(5) |
| b/Å | 9.378(6) |
| c/Å | 36.753(3) |
| $\alpha/°$ | 90.0 |
| $\beta/°$ | 90.0 |
| $\gamma/°$ | 90.0 |
| Volume/Å$^3$ | 2129.2(3) |
| Z | 4 |
| Density/gcm$^{-3}$ | 1.38 |
| Abs. Coeff/mm$^{-1}$ | 0.111 |
| F(000) | 1407.8 |
| $\theta_{min, max}$ | 2.2, 23.3 |
| $h_{min,max}, k_{min,max}, l_{min,max}$ | −9, 9; −10, 10; −36, 40 |

TABLE 1-continued

Single Crystal Parameters of S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

| DATA | Compound of the invention |
| --- | --- |
| No. Refl$^n$. measured | 18378 |
| No. unique Reflection | 4197 |
| No. parameters | 551 |
| Refinement method | Full matrix least square on F$^2$ |
| R_all | 0.062 |
| R_obs | 0.041 |
| wR$_2$ (all) | 0.072 |
| wR$_2$ (obs) | 0.067 |
| $\rho_{min,max}/eÅ^{-3}$ | −0.132, 0.132 |
| GooF | 1.064 |

The tests and procedures used to obtain the data included in Table 1 are standard in the art and a person skilled in the art would know how to carry out these tests based on this specification and his/her knowledge of the art.

Figure 2:
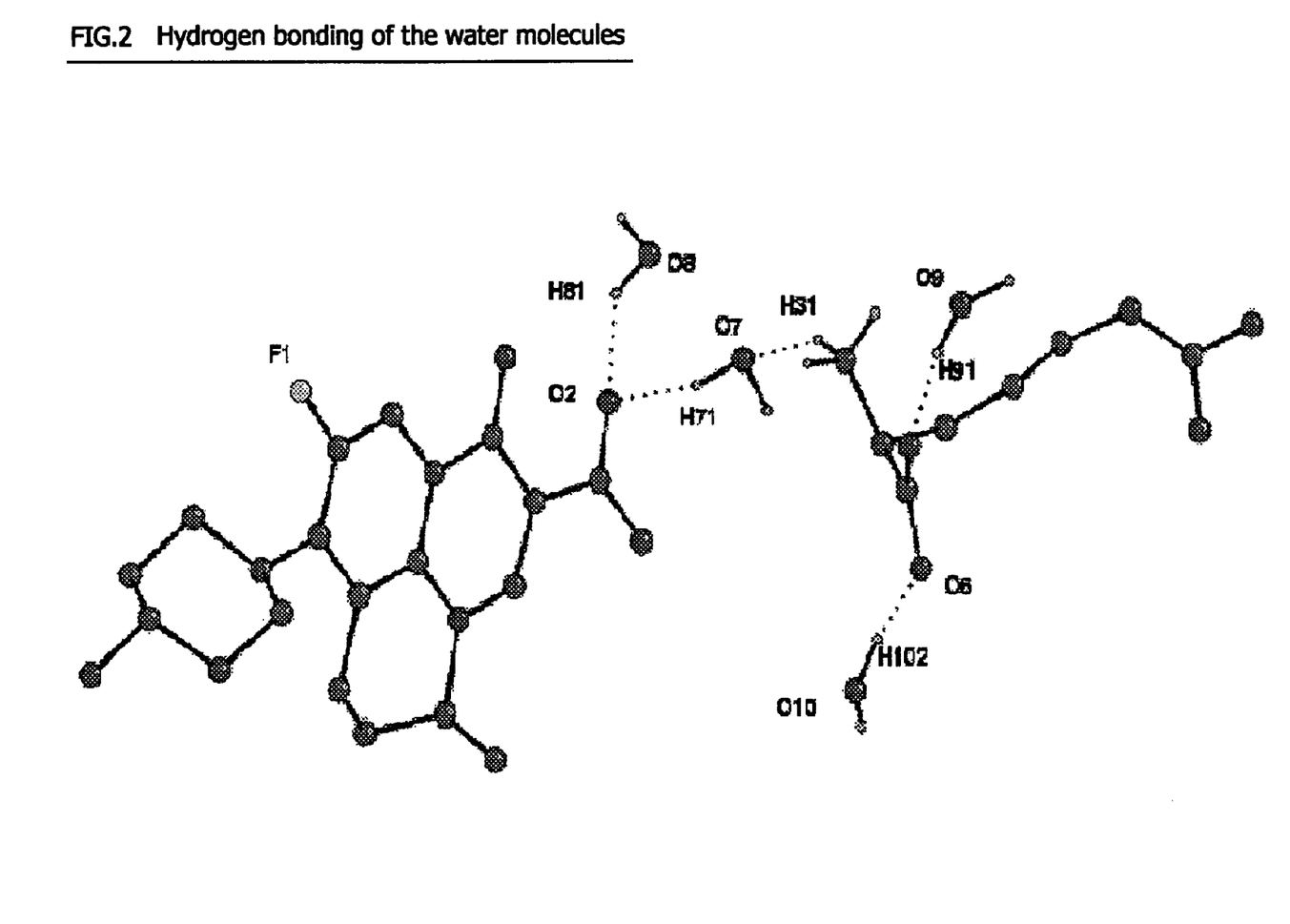
FIG. 2 shows the hydrogen bonding network of the water molecules in S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

The —COOH groups of both S-(−)-9-fluoro-6,7-dihydro-8-(4-hydroxypiperidin-1-yl)-5-methyl-1-oxo-1H,5H-benzo[i,j]quinolizine-2-carboxylic acid and L-arginine are found ionized as —COO$^-$ and H$^+$. These H$^+$ ions are taken up by the nitrogen lone pairs of L-arginine to form NH$_3^+$ and NH$_2^+$ respectively. The four water molecules were found to form strong hydrogen bonds with the —COO$^-$ groups (FIG. 2). In fact, H71 of one of the water molecules forms a strong O—H . . . O hydrogen bond with the —COO$^-$ group (H71 . . . O2 in FIG. 2) of the benzoquinolizine-2-carboxylic acid, along with yet another strong O . . . H—N hydrogen bond with —NH$_3^+$ group of L-arginine (O7 . . . H31 in FIG. 2). Thus, this water molecule (O7) bridges the two moieties resulting in a stronger association. However, the other three water molecules, two of which generate a strong O—H . . . O hydrogen bonds with the —COO$^-$ group of L-arginine (O9H01 . . . O5 and O10H102 . . . O6), and the remaining water molecule with —COO$^-$ of the benquinolizine-2-carboxylic acid (O8H81 . . . O2), are less tightly bound, all bindings being shown in FIG. 2. A Differential Scanning Calorimetric study (cf. FIG. 5) and Thermogravimetric Analysis (cf. FIG. 6) of the salt of the invention confirms the nature of binding, by three of the four water molecules (O8, O9 and O10) being lost on heating at 70° C., initially generating a monohydrate by retaining O7.

Crystalline S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt tetrahydrate with the water molecules bound as depicted by the single crystal x-ray analysis may be prepared in high homogeneity by the slow evaporation of the solution made by dissolving S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt in an organic solvent and water.

A process for the manufacture of the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate comprises the following consecutive steps:

a) heating a suspension of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt in an organic solvent and water at 70°–80° C. to obtain a clear solution;

b) cooling the solution to provide a crystalline substance;

c) isolating the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate at 30° C.–35° C. by filtration or centrifugation; and d) air drying of the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate at a temperature between 30° C.–35° C.

Any S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt can be used in step a).

The preferred organic solvents are acetonitrile and acetone. The most preferred organic solvent is acetone. The preferred ratio of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt to the organic solvent to water is 1:5:1.25 (w/v/v). The preferred ratio of acetone or acetonitrile to water is (4:1 v/v).

The solution of step a) is heated for as long as necessary to obtain a clear solution. A clear solution is typically obtained in 15 minutes to 3 hours but the time may vary.

In step b) the solution may be cooled to room temperature or between 30° C.–35° C.

Of the various crystalline forms of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt, the primary one that crystallizes directly from aqueous acetone solutions is the tetrahydrate. This tetrahydrate shows on Karl Fischer (KF) analysis a water content of 11.87%, (calculated for $4H_2O$: 11.88%), equivalent to four molecules of water of hydration. On further drying for 16 hrs at 70° C. and under high vacuum of 1 mm of Hg the tetrahydrate is converted to a monohydrate and analyses for a water content of 4.0%, (calculated for $1H_2O$: 3.98%).

Figure 3:
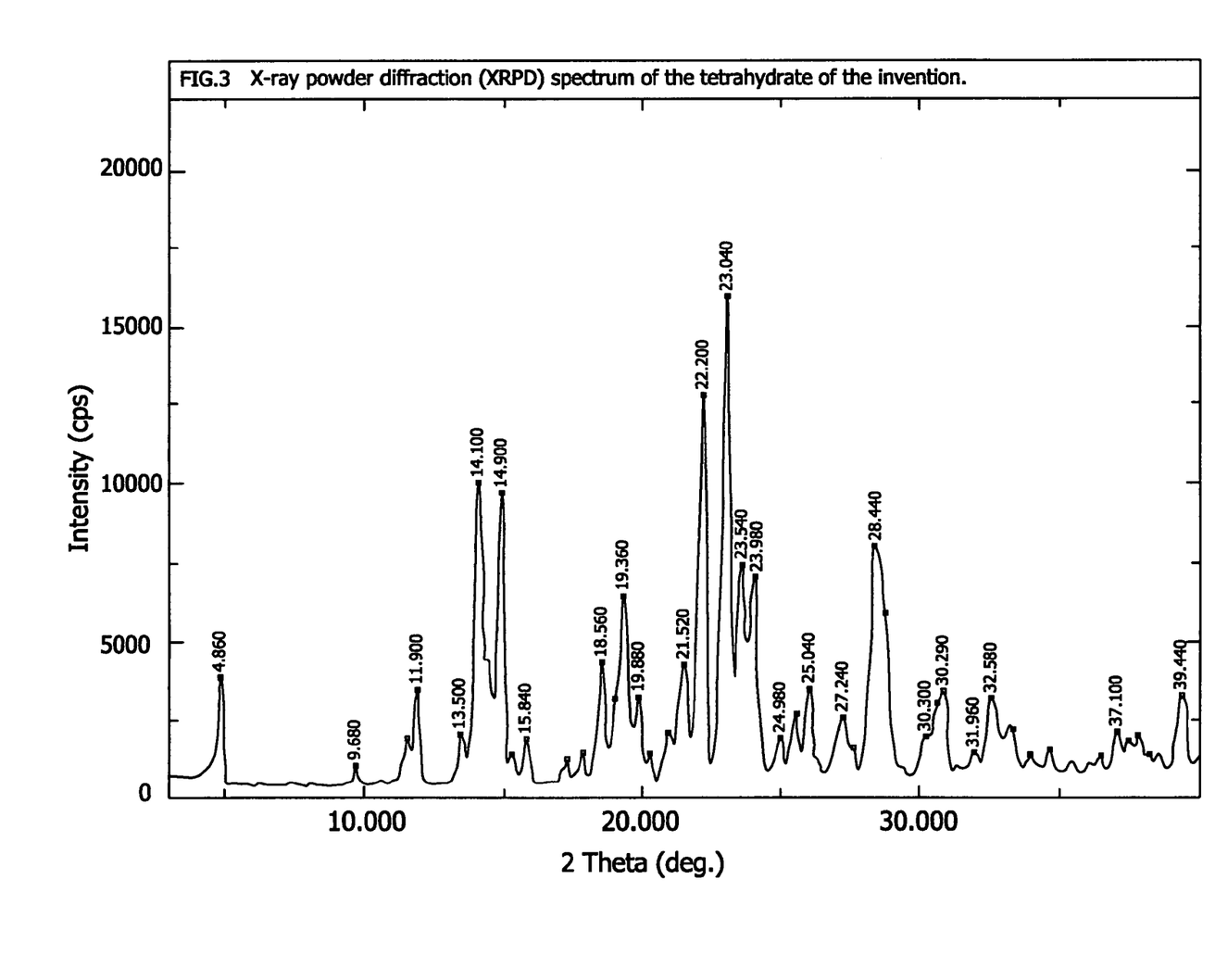
FIG. 3 is a X-ray Powder Diffraction (XRPD) pattern of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.
Figure 4:
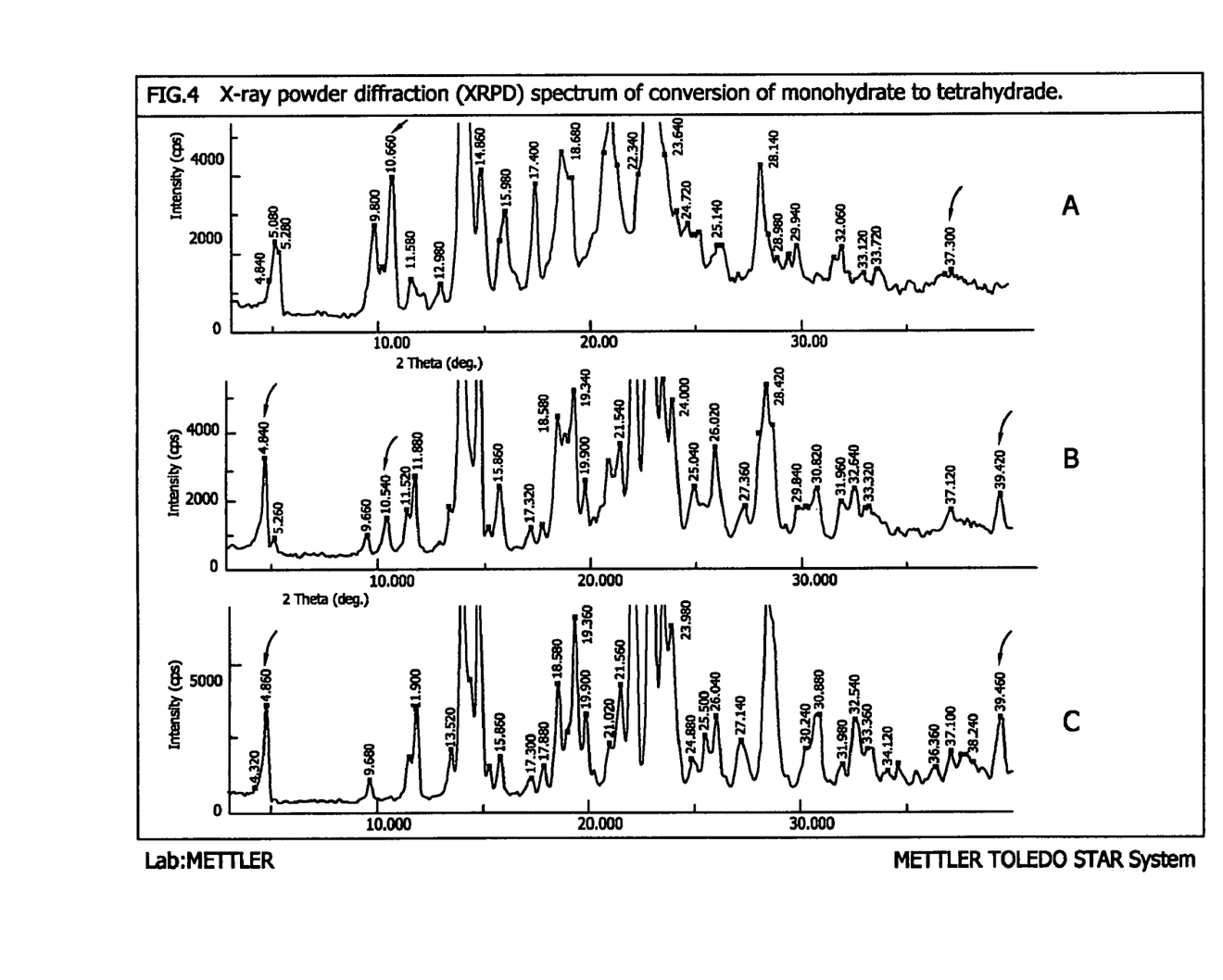
FIG. 4 is XRPD spectra illustrating conversion of monohydrate to tetrahydrate.

This monohydrate is highly unstable and rapidly absorbs moisture under ambient conditions of temperature (35° C.) and relative humidity (60%). Within 20 minutes the XRPD spectra of the monohydrate undergoes changes as illustrated by the diffractograms in FIG. 4, wherein the characteristic 2 θ peaks of the monohydrate appearing at 5.28 and 10.66 in FIG. 4-A shift to a reduction of the intensity of these peaks in FIG. 4-B with a concomitant appearance of peaks at 2 θ values of 4.84 and 39.2 which are characteristic of the tetrahydrate. In FIG. 4-C the total disappearance is seen of the peaks of the monohydrate. Its conversion to the tetrahydrate may be confirmed by the increase in the intensity of the 2 θ peaks at 4.84 and 39.42, peaks which overlap with those in FIG. 3 obtained for an authentic sample of the tetrahydrate.

Figure 7:
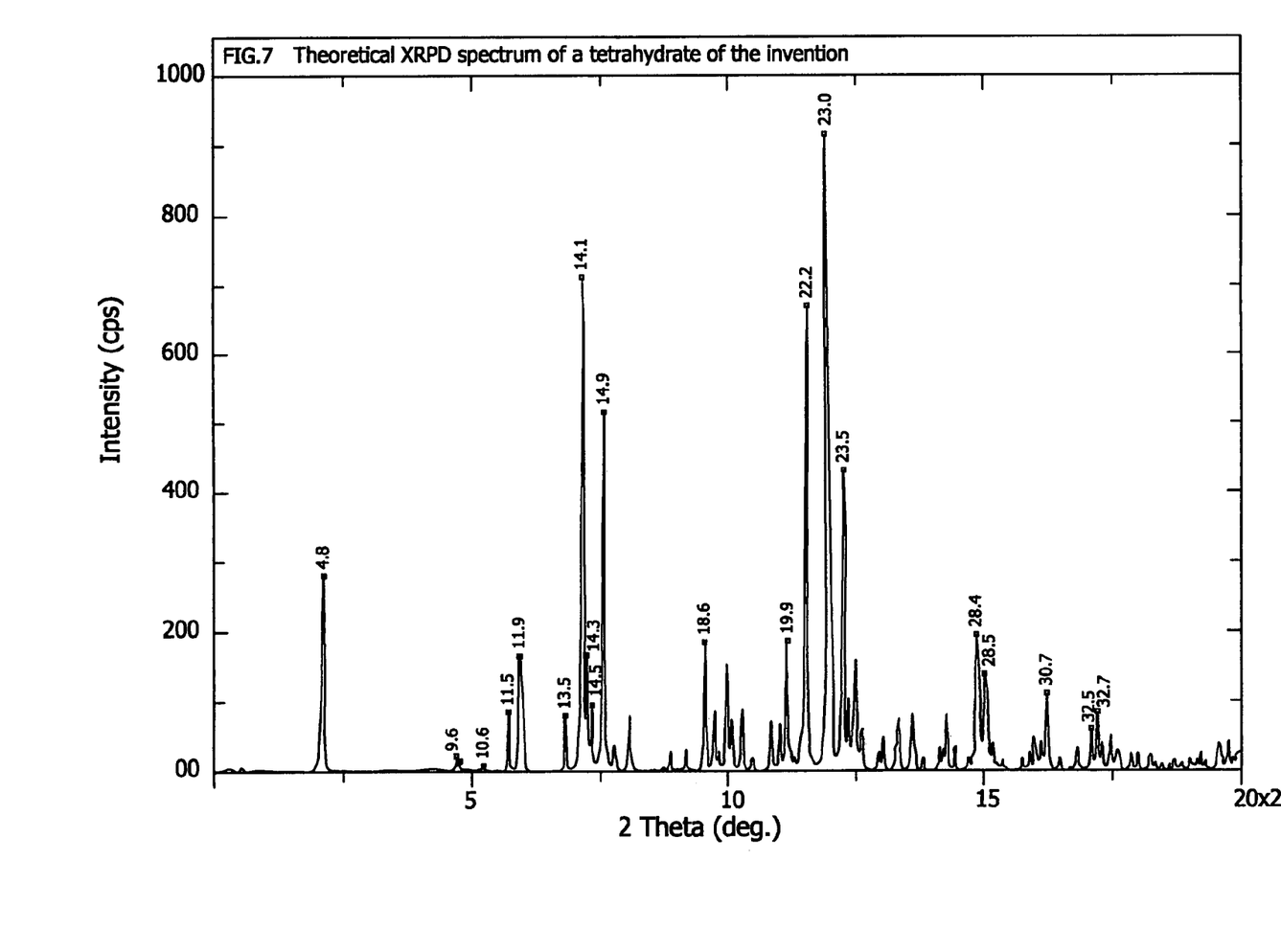
FIG. 7 is theoretical XRPD spectrum calculated by a standard software from the coordinates of a single crystal X-ray analysis.

The high homogeneity of the prepared tetrahydrate may be confirmed by comparison of its XRPD spectrum (FIG. 3) with that obtained theoretically for single phase tetrahydrate material (FIG. 7) by inserting the coordinates derived from a single crystal X-ray structure into a standard software programme. The XRPD spectrum in FIG. 3 is seen to be identical with that provided in FIG. 7.

The water content of the tetrahydrate may range from 11.0 to 12.5% according to the Karl Fischer analysis.

This novel crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt of this invention is stable under typical storage conditions, has good bioavailability in mammals, has lower phlebitis-forming potential on administration to mammals, has low or reduced toxicity, has acceptable disintegration and dissolution rates, and hence is very useful for pharmaceutical manufacturing and for use in medicine. Formulation of the thermodynamically most stable form is a reasonable expectation for a solution mediated process. Using the most stable form rather than a metastable form is advantageous regarding physical stability of the crystalline form. The increased physical stability will afford additional advantages in formulation. The form is specially suitable for treating diseases caused by microbial infections. The form is suitable for long-term intravenous therapy in critically ill patients or patients in intensive care units. Injectable preparations of the L-arginine salt can be readily prepared in view of its availability in a bulk form that remains stable under specified conditions, its favorable aqueous solubility, its ideal suitability in not causing venous inflammation on repeated intravenous administration, and its safety from adverse toxicity.

The antibacterial polymorphic compound of the invention is useful in the treatment of mammals having a broad spectrum of bacterial infections such as impetigo, pneumonia, bronchitis, pharyngitis, endocarditis, urinary tract infections, gastro-intestinal infections and bacteremias caused by *Staphylococcus aureus*, coagulase negative staphylococci, methicillin-resitant *Staphylococcus aureus*, methicillin-resistant coagulase negative staphylococci, enterococci, beta-haemolytic streptococci, viridans group of streptococci, mycobacterial infections due to multi-drug resistant *M. tuberculosis* and other atypical mycobacteria such as *M. intracellulare* and *M. avium*, as well as newly emerging Gram-negative pathogens such as *Chryseobacterium meningosepticum*, *Chryseobacterium indologense* and other Gram-negative pathogens such as *E. coli*, *Klebsiella*, *Proteus*, *Serratia*, *Citrobacter*, and *Pseudomonas*.

The present invention also encompasses an antiinfective composition for the treatment of humans and animals in need of prophylaxis and/or therapy for systemic or topical infections especially resistant gram-positive organism infections, gram-negative organism infections, mycobacterial infections and nosocomial pathogen infections, which composition comprises an amount of the compound of the invention substantially sufficient to eradicate said infection, but not to cause any undue side effects. The compound and compositions of this invention can be administered to humans and animals who are at risk of being infected, for example a compound or composition of this invention can be administered to a patient prior to and/or after surgery, health care workers or others who are at risk of being infected.

These findings have an important implication from the point of view of the systemic use of the compound of the invention in view of its superior potency, superior bactericidal activity, expanded biospectrum, better bioavailability and improved tolerability which are now enabled to be administered systemically in therapeutically effective doses. Utilizing the compound of the invention, whether in systemic or topical dosage form, results in clearer dose-related definitions of efficacy, diminished toxic effects and accordingly an improved therapeutic index.

The present invention encompasses the compound of administering the compounds to a human or other animal subject. The compound and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions are prepared according to conventional procedures used by persons skilled in the art to make stable and effective compositions. Such methods include combining the tetrahydrate of this invention with suitable a carrier, diluent, solvent or excipient. In the solid, liquid, parenteral and topical dosage forms, an effective amount of the active compound or the active ingredient is any amount, which produces the desired results.

It has been found in accordance with the present invention that the advantageous stability and solubility properties of the tetrahydrate of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt can be applied to the formulation of pharmaceutical dosage forms. Tables providing stability and solubility data are included in the examples. The tetrahydrate of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt can be used to prepare aqueous dosage forms. It can also be used to prepare tablets by wet granulation; it can also be formulated by conventional dry granulation.

The dosage forms can be prepared by any conventional techniques recognized in the art, but would preferably be formulated by mixing the tetrahydrate salt of the invention with the other ingredients. The other ingredients utilized to formulate solid oral dosage forms would include conventional inert ingredients such as microcrystalline cellulose, methyl cellulose and the like, suitable sweetening and/or flavouring agents, and preservatives thereof if required.

Such solid oral dosage forms or dry formulations suitable for the preparation of suspensions would be formulated such that they would contain an effective dose of the compound of the invention. In general, solid dosage forms containing 100 mg–1500 mg of the compound of the invention are contemplated. Preparations suitable for oral suspension would contain a similar dosage.

Pharmaceutical formulations can be formulated together with auxiliaries and additives usually employed in pharmacy, such as tablet binders, fillers, preservatives, tablet disintegrating agents, flow regulating, agents, plasticizers, wetting agents, dispersing agents, emulsifiers, solvents, pH altering additives, flavourings and the like. A second preferred method is parenterally for intramuscular, intravenous or subcutaneous administration.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

It is preferred that the concentration of active ingredient in the injectable preparation be in the range of 0.1 mg/ml to 100 mg/ml.

A third preferred route of administration is topically, for which creams, ointments, sprays, shampoos, lotions, gels, dusting powders and the like are well suited. Generally, an effective amount of the compound according to this invention in a topical form 0.1% composition is to about 10% by weight of the total composition. Preferably, the effective amount is 1% of the total composition.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

The total daily dose range is generally from about 200 mg to about 1500 mg of the arginine salt form. However, the dose may be higher or lower depending on the needs and conditions of the patient.

The following detailed examples serve to more fully illustrate the invention without limiting its scope. It is understood that various other embodiments and modifications in the practice of the invention will be apparent to, and can be readily made by, those or ordinary skill in the art without departing from the scope and spirit of the invention as described above. Accordingly, it is not intended that the scope of the claims appended hereto be limited to the exact description set forth above, but rather than the claims be construed as encompassing all of the features of patentable novelty that reside in the present invention, including all of the features and embodiments that would be treated as equivalents thereof by those skilled in the relevant art. The invention is further described with reference to the following experimental work.

EXAMPLE 1

Figure 1:
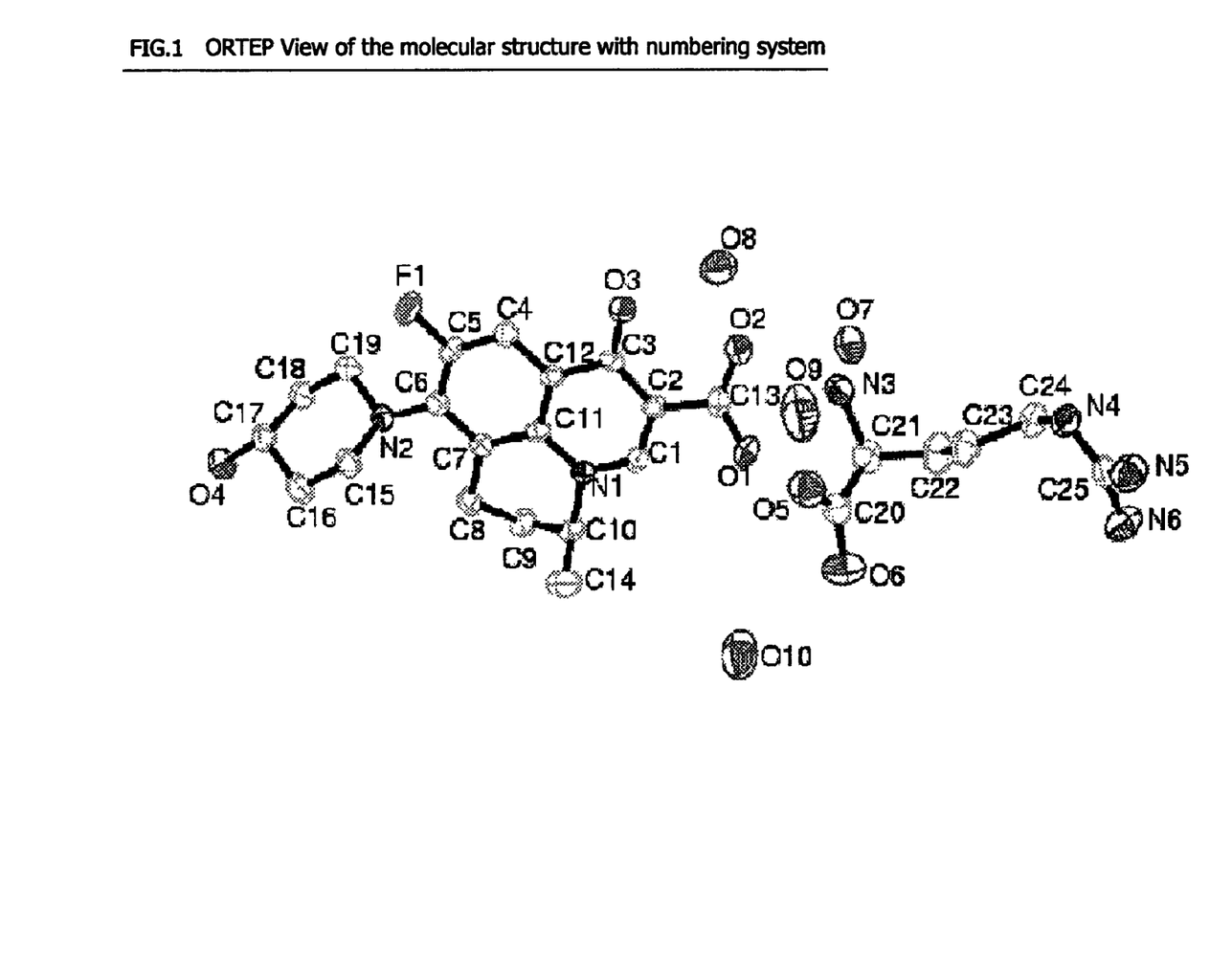
FIG. 1 shows the single crystal X-ray ORTEP diagram of the of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

Preparation of the Single Crystal of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt terahydrate S-(−)-9-Fluoro-6,7-dihydro-8-(4-hydroxypiperidin-1-yl)-5-methyl-1-oxo-1H,5H-benzo[i,j]quinolizine-2-carboxylic acid L-arginine salt (1.0 g) was dissolved in a mixture of acetone (40 ml) and water (10 ml) by heating the suspension at 70° C. for 15 minutes. The clear solution thus obtained was left for slow evaporation at room temperature in a beaker covered with a perforated aluminum foil. The crystal formation started after 2 days. Finally the single crystal was selected for X-ray crystal analysis from a cluster left after complete evaporation of the solvent. The ORTEP diagrams are described in FIGS. 1 and 2.

EXAMPLE 2

Larger Scale Preparation of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt terahydrate To a three-necked round bottom flask fitted on oil bath and equipped with magnetic stirrer and reflux condenser; S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt (20.0 gm, 55.55 mmoles) was charged in a mixture of acetone (100 ml) and water (25 ml). The reaction mixture was slowly heated under stirring at 70° C. temperature to obtain a clear solution. The solution was allowed to cool to 30° C.–35° C., a crystalline solid obtained was filtered and air dried at a temperature between 30° C.–35° C. to afford the title compound 23.5 gm, (80%). The moisture content by Karl Fisher titration was found to be 11.87% (required for tetrahydrate: 11.88%). The XRPD, DSC, TGA data were determined as described in the Test Examples provided below. The results obtained are described in FIGS. 3, 5, 6.

TEST EXAMPLE 1

Single Crystal X-Ray Analysis

The room temperature single crystal X-ray diffraction data on a prism shaped single crystal were collected on a Bruker AXS single crystal X-ray diffractometer using SMART APEX CCD detector at room temperature [293(2)° K]. The X-ray generator was operated at 50 KV and 35 mA using MoK$_\alpha$ radiation. Data were collected with a ω scan width of 0.3°. A total of 606 frames per sets were collected in three different settings of φ (0°, 90° and 180°) keeping the sample to detector distance of 6.03 cm and the 2θ-value fixed at −25°. The data were reduced by SAINTPLUS [Bruker. SMART, SAINT, SADABS, XPREP, SHELXTL. Bruker AXS Inc. Madison. Wis., USA. 1998] and an empirical absorption correction was applied using the package SADABS [Bruker. SMART, SAINT, SADABS, XPREP, SHELXTL. Bruker AXS Inc. Madison. Wis., USA. 1998]. All the structures were solved using SIR92 [Altomare, A.; Cascarano, G.; Giacovazzo, C.; Guagliardi, A. SIR92— A program for crystal structure solution. J. Appl. Crystallogr. 1993, 26, 343.] and refined using SHELXL97 [Sheldrick G. M. SHELXL97, Program for crystal structure refinement, University of Göttingen, Germany. 1997.].

Molecular and packing diagrams were generated by ORTEP32 [Farrugia, L. J. J. Appl. Cryst. 1997, 30, 565.] and CAMERON [Watkin, D. M.; Pearce, L.; Prout, C. K. CAMERON—A Molecular Graphics Package. Chemical Crystallography Laboratory, University of Oxford, England. 1993.] present in the WINGX (Version 1.64.03b) [Farrugia, L. J. WINGX. J. Appl. Cryst. 1999, 32, 837.] program suite. The geometric calculations were done by PARST95 [Nardelli, M. J. Appl. Cryst. 1995, 28, 569.] and PLATON97 [Spek, A. L. Acta Crystallogr. Sect A 1990, 46, C34.].

The ORTEP diagram of the single crystal (FIG. 1) shows the four water molecules.

The product was analysed for moisture content (12.37%) by KF titration.

TEST EXAMPLE 2

Powder X-ray Diffraction Analysis 300 mg of S-(−)-9-fluoro-6,7-dihydro-8-(4-hydroxypiperidin-1-yl)-5-methyl-1-oxo-1H,5H-benzo[I,j]quinolizine-2-carboxylic acid L-arginine salt tetrahydrate prepared as in Example 1 was thinly spread on a sample holder. X-ray diffraction analyses (40 kv x 40 mA Rigaku D/max 2200) were performed under the conditions listed below:
Scan speed 5°/min or 20°/min
Sampling time 7 min or 2 min
Scan mode: continuous
2θ/θ reflection
Cu target (Ni filter)

The X-ray powder diffraction (XRPD) spectra of the title compound is shown in FIG. 3.

(2θ):4.86±0.2, 14.10±0.2, 14.90±0.2, 19.35±0.2, 22.20±0.2, 23.04±0.2, 23.54±0.2, 28.44±0.2, 39.44±0.2.

The X-ray powder diffraction (XRPD) spectra of the monohydrate, the tetrahydrate and a mixture thereof is shown in FIG. 4.

TEST EXAMPLE 3

Differential Scanning Calorimetry

The Differential Scanning Calorimetry (DSC) was recorded on METTLER TOLEDO STAR system. 5 to 6 mg of the sample was weighed into the aluminum pan, which was then press sealed with an aluminium lid. After three tiny needle holes were made on the lid the sample was tested by heating from 30° C. to 300° C. at a rate of 10° C./min.

Figure 5:
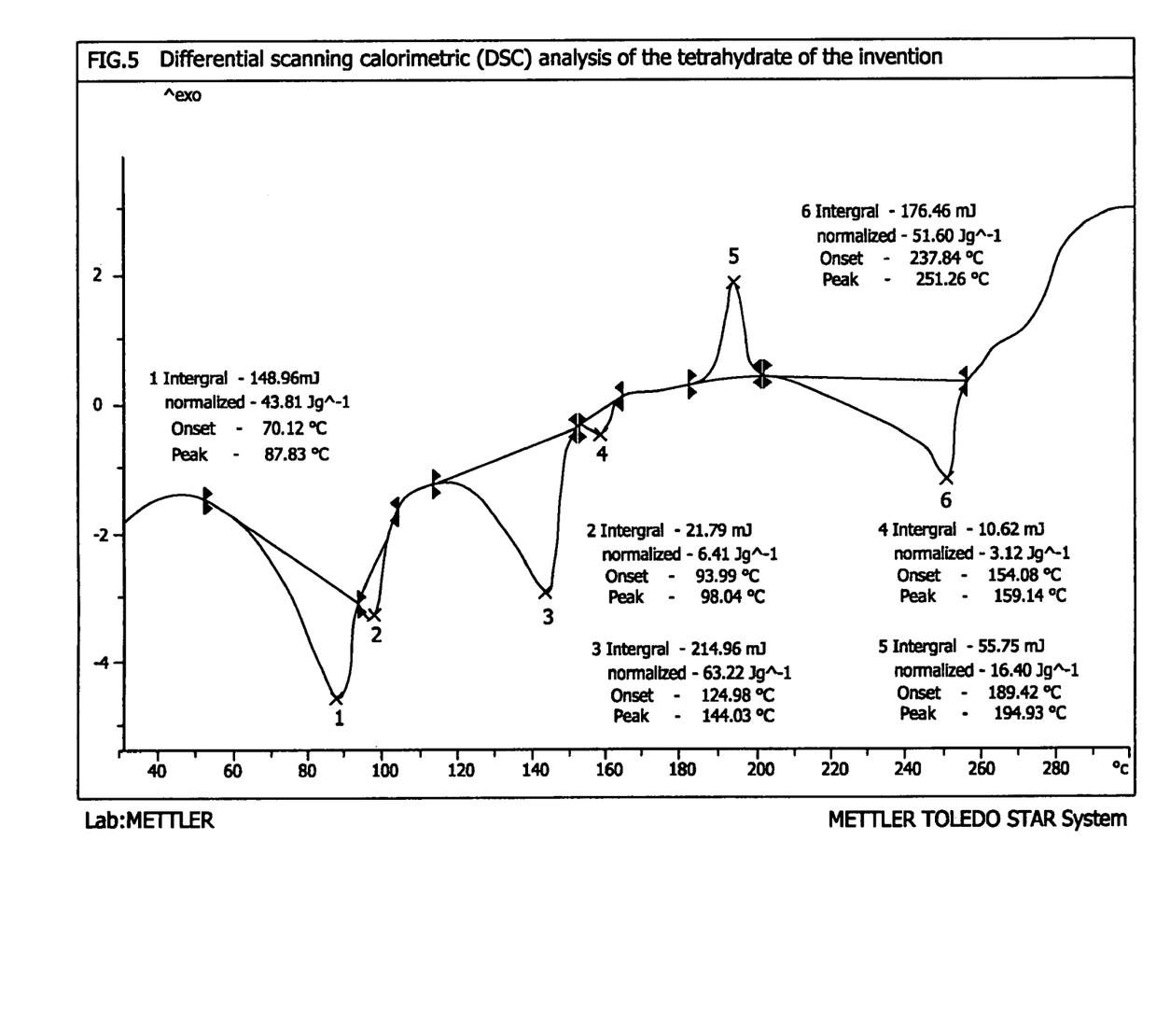
FIG. 5 is a Differential Scanning Calorimeter (DSC) analysis of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

The differential scanning calorimetry (DSC) analysis of the title compound is shown in FIG. 5. A DSC exotherm at 194.93° C. (onset at 189.42° C.) and one endotherm at 87.83° C., 144.03° C. and 251.26° C.

TEST EXAMPLE 4

Thermogravimetric Analysis

Thermogravimetric Analysis (TGA) was recorded on a METTLER TOLEDO TGA/SDTA 851 system. 5 to 10 mg of the sample was weighed into the aluminum pan and sample was tested by heating from 30° C. to 300° C. at a rate of 10° C./min.

Figure 6:
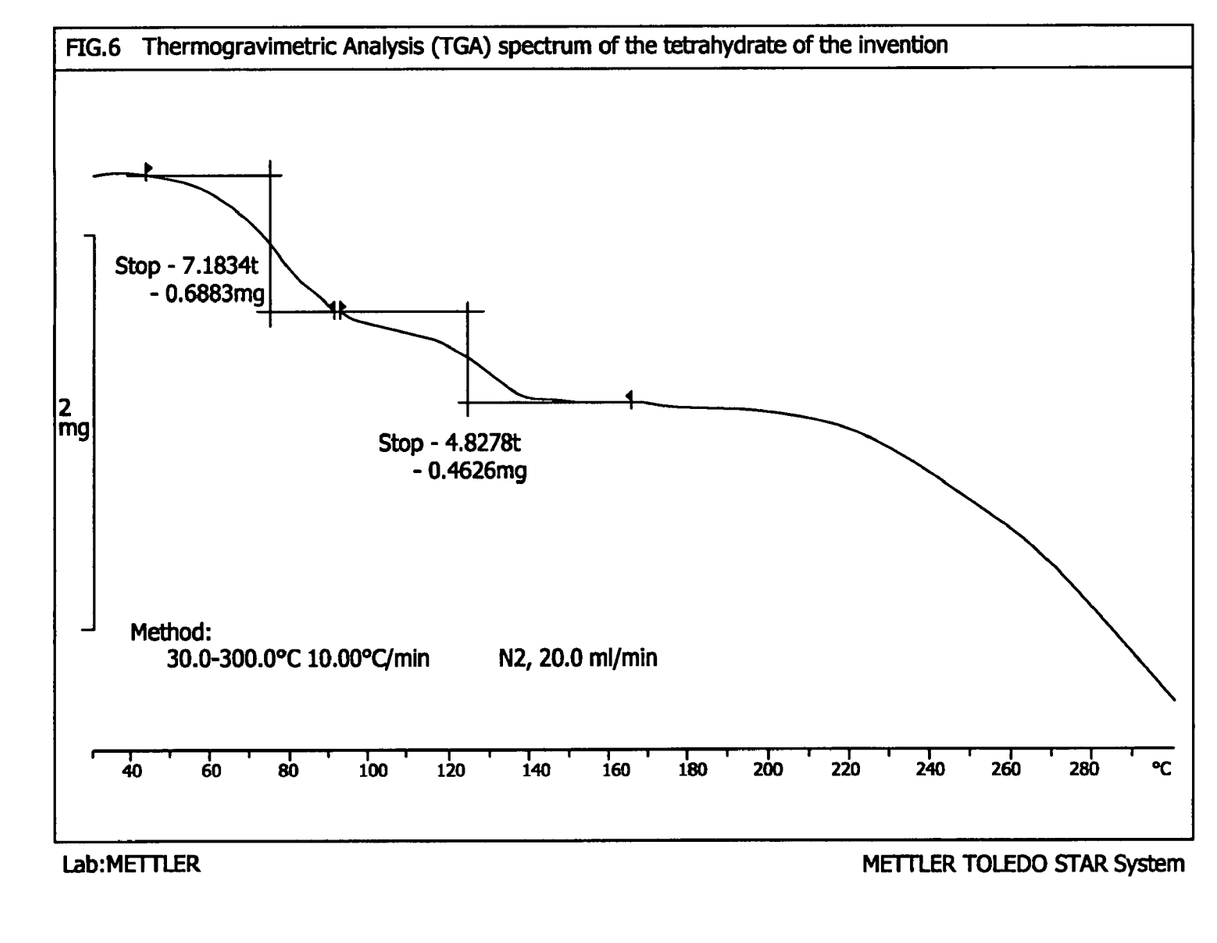
FIG. 6 is a thermogravimetric analysis of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate.

The thermogravimetric analysis (TGA) of the title compound is shown in FIG. 6.

TEST EXAMPLE 5 pH-Related Solublility of S-(−)-9-fluoro-6,7-dihydro-8-(4-hydroxypiperidin-1-yl)-5-methyl-1-oxo-1H, 5H-benzo[I,j]quinolizine-2-carboxylic acid L-arginine salt tetrahydrate at 30° C.

An accurately weighed amount about 20 mg of the compound was transferred to a conical flask and a buffer solution of appropriate pH was added in portions (0.2 ml at a time) till a clear solution was obtained. At buffer pH values of 8.0 and 8.5 addition of buffer was discontinued at 20 ml.

| pH of buffer | Solubility (mg/ml) |
|---|---|
| 8.0 | <1.0 |
| 8.5 | <1.0 |
| 9.0 | 2.0 |
| 9.5 | 5.0 |

TEST EXAMPLE 6

Temperature/Relative Humidity-Related Stability of S-(−)-9-fluoro-6,7-dihydro-8-(4-hydroxypiperidin-1-yl)-5-methyl-1-oxo-1H,5H-benzo[I,j]quinolizine-2-carboxylic acid L-arginine salt tetrahydrate

3 Sample batches of the compound were stored under the conditions of the study as stated in the table below. The assay was done by a validated HPLC method. The results are provided in the table below.

| Temp.(° C.)/ | Time (months) | | | |
|---|---|---|---|---|
| Relative Humidity (%) | Initial | 1 | 2 | 3 |
| 40/75 | 99.31% | 99.30% | 99.25% | 99.27% |
| 25/60 | 99.31% | — | — | 99.22% |

The crystallinity of the substance underwent no changes as seen by XRPD spectra.

The invention claimed is:

1. S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate of the formula I Formula I in a crystalline form.

2. A S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate having the following X-ray powder diffraction data: (2θ):4.86±0.2, 14.10±0.2, 14.90±0.2, 19.35±0.2, 22.20±0.2, 23.04±0.2, 23.54±0.2, 28.44±0.2, 39.44±0.2.

3. A S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate having the following X-ray powder diffraction data: (2θ):4.86±0.2, 14.10±0.2, 14.90±0.2, 19.35±0.2, 22.20±0.2, 23.04±0.2, 23.54±0.2, 28.44±0.2, 39.44±0.2.; a DSC exotherm at 194. 93° C. (onset at 189.42° C.) and one endotherm at 87.83° C., 144.03° C. and 251.26° C. and a water content of between 11.0 to 12.5% as determined by titration according to Karl Fischer.

4. The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate according to claim 2, having a DSC exotherm at 194. 93° C. (onset at 189.42° C.) and one endotherm at 87.83° C., 144.03° C. and 251.26° C.

5. The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate according to claim 2, wherein the solubility in a solution of pH 9.5 is 5.0 mg/ml.

6. The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate according to claim 3, wherein the solubility in a solution of pH 9.5 is 5.0 mg/ml.

7. The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate according to claim 1, wherein the water content is between 11.0% and 12.5% by weight as determined by titration according to Karl Fischer.

8. The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt tetrahydrate according to claim 2, wherein the water content is between 11.0% and 12.5% by weight as determined by titration according to Karl Fischer.

9. A process for the manufacture of S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt tetrahydrate comprising the steps of:
   a) heating a suspension of S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt tetrahydrate in an organic solvent and water at 70–80° C. to obtain a clear solution;
   b) cooling the solution to provide a crystalline substance;
   c) isolating the crystalline form of S-(−)-9-fluoro-6,7-dihydro-8-(4-hydroxypiperidin-1-yl)-5-methyl-1-oxo-1H, 5H-benzo[i,j]quinolizine-2-carboxylic acid L-arginine salt tetrahydrate tetrahydrate at 30° C.–35° C. by filtration or centrifugation;
   d) air drying of the crystalline form of S-(−)-9-fluoro-6, 7-dihydro-8-(4-hydroxypiperidin-1-yl)-5-methyl-1-oxo-1H,5H-benzo[i,j]quinolizine-2-carboxylic acid L-arginine salt tetrahydrate tetrahydrate at a temperature between 30° C.–35° C.

10. A process according to claim 9, wherein the organic solvent is acetone or acetonitrile.

11. The process according to claim 9 wherein the organic solvent is acetone.

* * * * *